(12) United States Patent
Girschweiler et al.

(10) Patent No.: US 11,009,026 B2
(45) Date of Patent: May 18, 2021

(54) MICROPUMP

(71) Applicant: SENSILE MEDICAL AG, Olten (CH)

(72) Inventors: Michael Girschweiler, Ziefen (CH); Alexandre Perrier, Liestal (CH)

(73) Assignee: SENSILE MEDICAL AG, Olten (CH)

( * ) Notice: Subject to any disclaimer, the term of this patent is extended or adjusted under 35 U.S.C. 154(b) by 0 days.

(21) Appl. No.: 16/770,111

(22) PCT Filed: Dec. 2, 2018

(86) PCT No.: PCT/EP2018/083247
§ 371 (c)(1),
(2) Date: Jun. 5, 2020

(87) PCT Pub. No.: WO2019/110455
PCT Pub. Date: Jun. 13, 2019

(65) Prior Publication Data
US 2020/0378387 A1  Dec. 3, 2020

(30) Foreign Application Priority Data

Dec. 6, 2017 (EP) ..................................... 17205753

(51) Int. Cl.
*F04D 15/00* (2006.01)
*F04D 1/00* (2006.01)
(Continued)

(52) U.S. Cl.
CPC ........... *F04D 15/0005* (2013.01); *F04D 1/00* (2013.01); *F04D 29/086* (2013.01); *A61M 5/14212* (2013.01); *A61M 5/16804* (2013.01)

(58) Field of Classification Search
None
See application file for complete search history.

(56) References Cited

U.S. PATENT DOCUMENTS 7,726,955 B2  6/2010  Ryser et al.
8,282,366 B2 * 10/2012  Hilber .................... F04B 51/00
                                                    417/420
(Continued)

FOREIGN PATENT DOCUMENTS

DE  10 2011 08357  11/2012
EP  1 677 859  7/2006
EP  1 803 934  7/2007

OTHER PUBLICATIONS

Written Opinion in International Application No. PCT/EP2018/083247, dated Jan. 21, 2019, pp. 1-7.

*Primary Examiner* — Michael Lebentritt
*Assistant Examiner* — Jason G Davis
(74) *Attorney, Agent, or Firm* — Saliwanchik, Lloyd & Eisenschenk

(57) ABSTRACT

A pump includes: a stator (4), a rotor (6) slidably and rotatably mounted at least partially in the stator, the rotor comprising a first axial extension (24) having a first diameter (D1) and a second axial extension (26) having a second diameter (D2) greater than the first diameter, a first valve (V1) formed by a first valve seal (18) mounted on the stator around the first axial extension, in conjunction with a first channel (42) in the rotor that is configured to allow liquid communication across the first valve seal when the first valve is in an open position, a second valve (V2) formed by a second valve seal (20) mounted on the stator around the second axial extension, in conjunction with a second channel (44) in the rotor that is configured to allow liquid communication across the second valve seal when the second valve is in an open position; a pump chamber (8) formed between the rotor (6) and stator (4) and between the first valve seal (18) and second valve seal (20); and a pump chamber seal (22) circumscribing the rotor second axial extension and separating the pump chamber (8) from an (Continued)

external environment. The stator (4) further comprises a dead-zone seal section (40) surrounding a dead-zone volume (39) formed between the rotor second axial extension (26) and the stator (4), wherein the dead-zone seal section (40) comprises axially extending portions (58) connected to upper and lower radial portions (60,60') to form a closed sealing circuit.

11 Claims, 6 Drawing Sheets

(51) Int. Cl.
 *F04D 29/08* (2006.01)
 *A61M 5/142* (2006.01)
 *A61M 5/168* (2006.01)

(56) References Cited

U.S. PATENT DOCUMENTS

| | | |
|---|---|---|
| 9,222,470 B2 * | 12/2015 | Genoud ............ A61M 5/14216 |
| 10,213,796 B2 | 2/2019 | Frey |
| 2013/0017099 A1 | 1/2013 | Genoud et al. |
| 2018/0036750 A1 | 2/2018 | Frey |

\* cited by examiner

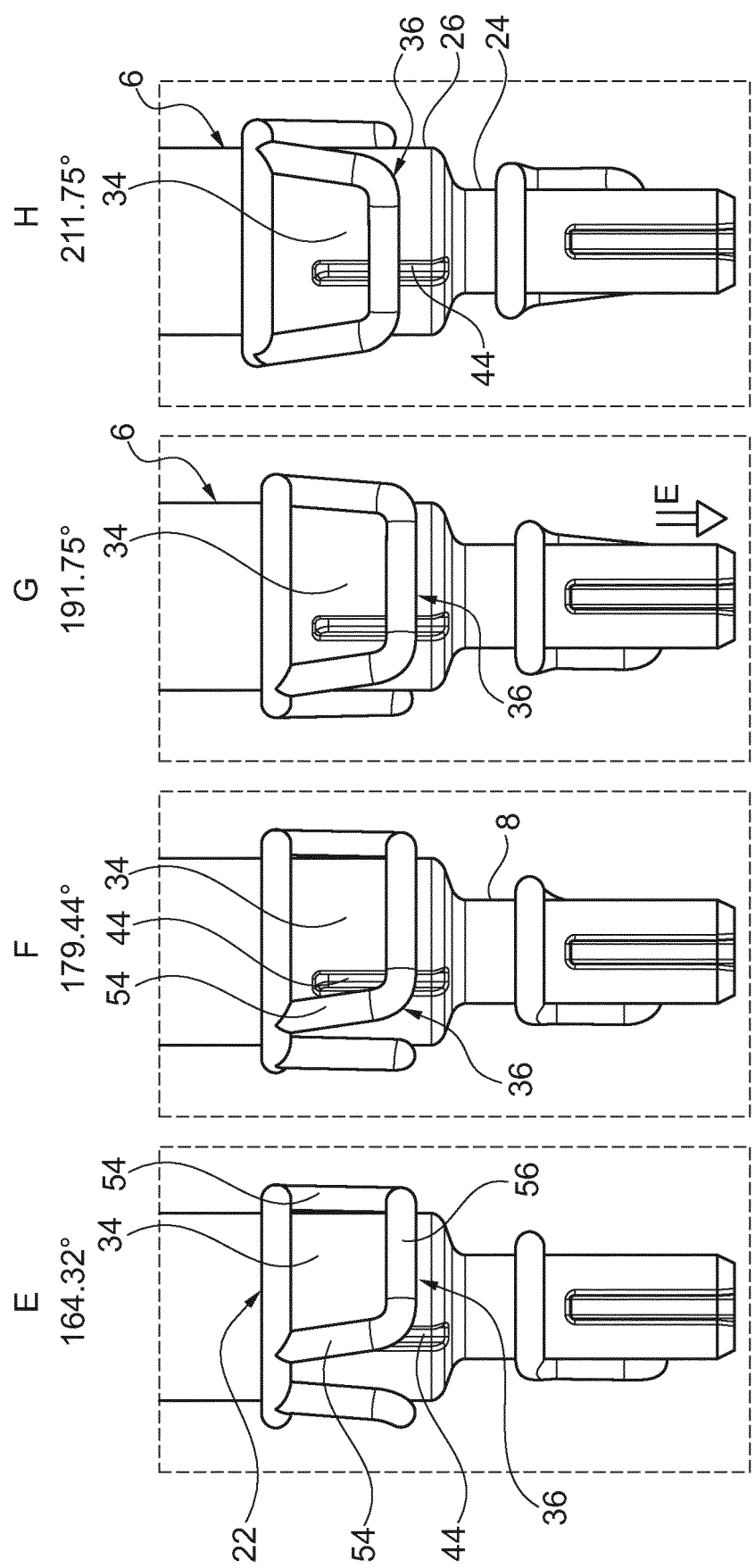
Fig. 3cont.

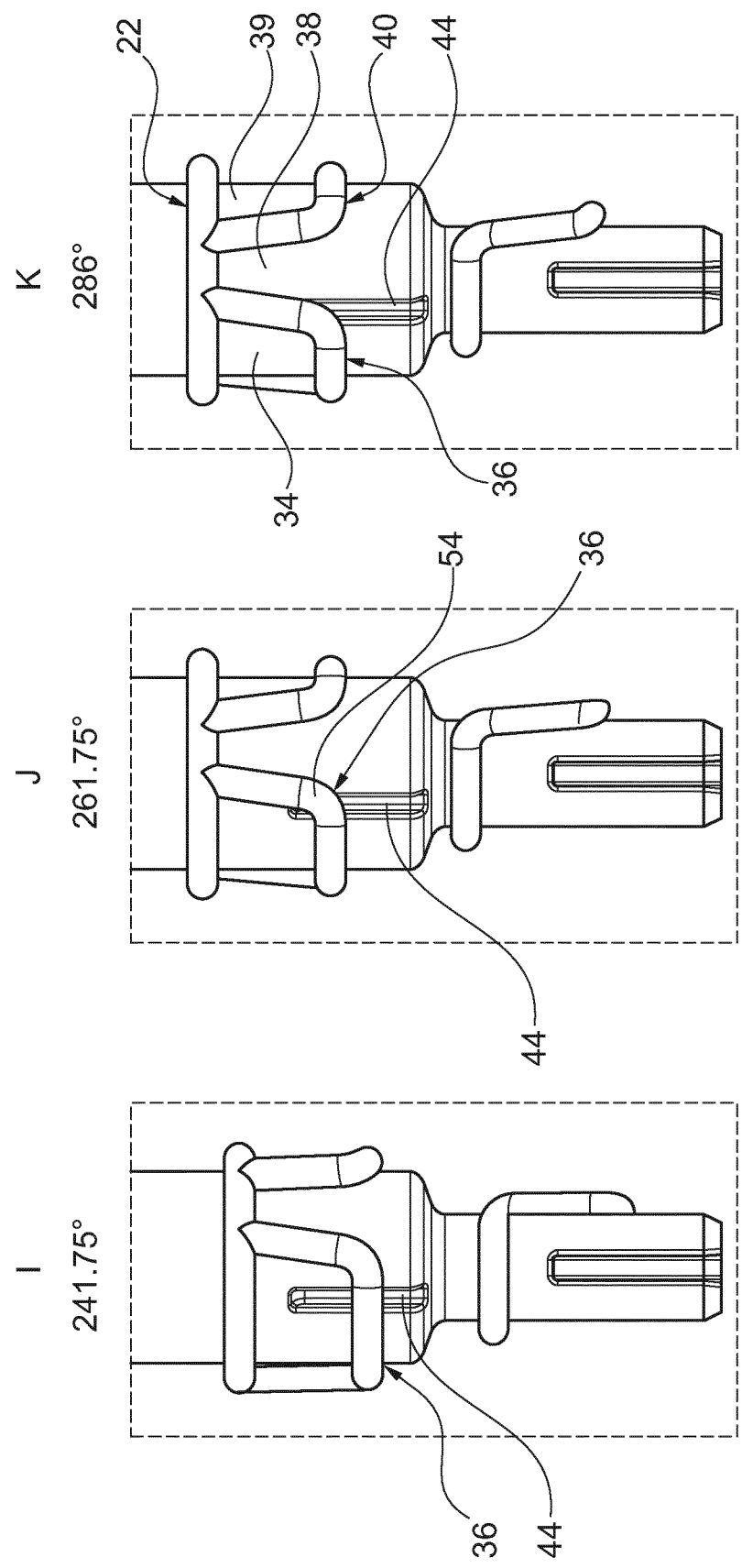

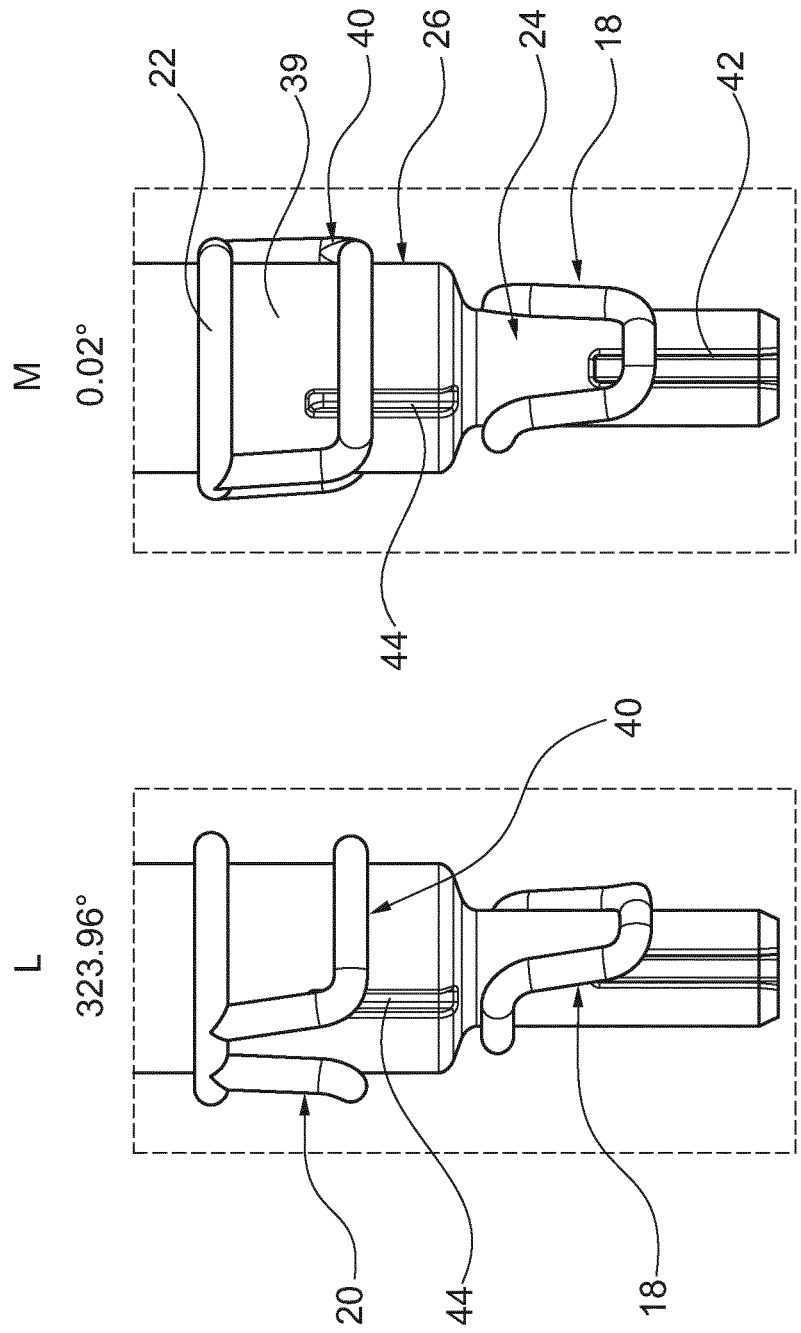
Fig. 3cont.

MICROPUMP

CROSS-REFERENCE TO RELATED APPLICATION

This application is the U.S. national stage application of International Patent Application No. PCT/EP2018/083247, filed Dec. 2, 2018.

TECHNICAL FIELD

The present invention relates to a micropump. The micropump may be used for dispensing small quantities of liquid, in particular for use in medical applications, for instance in a drug delivery device. A micropump related to the invention may also be used in non-medical applications that require high precision delivery of small quantities of liquid.

DESCRIPTION OF RELATED ART

A micropump for delivering small quantities of liquid that may in particular be used in medical and non-medical applications is described in EP1803934 and in EP1677859. The micropump described in the aforementioned documents includes a rotor with first and second axial extensions of different diameters that engage with first and second seals of the stator to create first and second valves that open and close liquid communication across the respective seal as a function of the angular and axial displacement of the rotor. A pump chamber is formed between the first and second seals of the stator whereby the pumped volume of liquid per rotation cycle of the rotor is a function of both the difference in diameters between the first and second rotor axial extensions and the axial displacement of the rotor that is effected by a cam system as a function of the angular position of the rotor with respect to the stator. The ability to control the pumped volume per cycle as a function of the rotary and axial displacement of the rotor but also the difference in diameters between the rotary extensions enables to pump very small quantities of liquid per revolution of the rotor with high accuracy.

Despite the accuracy of the aforementioned known pumps, there is a continuous need to improve accuracy and reliability of micropumps considering operating conditions (temperature, pressure, rate of flow) and the properties of the liquid. One of the factors that may affect pump accuracy is the presence of gas bubbles within the pump chamber. During expulsion of liquid from the pump chamber, the presence of a gas bubble reduces the actual volume of liquid being pumped, even if the gas bubble is in a dead-zone portion of the pump chamber due to the compressibility of the gas. The gas bubble may originate from air that is trapped inside the micropump before first use thereof, or originate from the liquid to be pumped.

SUMMARY OF THE INVENTION

In view of the foregoing, an object of the invention is to provide a micropump with improved accuracy taking into account the possible presence or formation of gas within the pump chamber.

Objects of the invention are achieved by a micropump according to claim 1.

Disclosed herein is a pump including
a stator,
a rotor slidably and rotatably mounted at least partially in the stator, the rotor comprising a first axial extension having a first diameter and a second axial extension having a second diameter greater than the first diameter,
a first valve formed by a first valve seal mounted on the stator around the first axial extension, in conjunction with a first channel in the rotor that is configured to allow liquid communication across the first valve seal when the first valve is in an open position,
a second valve formed by a second valve seal mounted on the stator around the second axial extension, in conjunction with a second channel in the rotor that is configured to allow liquid communication across the second valve seal when the second valve is in an open position, and
a pump chamber formed between the rotor and stator and between the first valve seal and second valve seal.

The stator further comprises a dead-zone seal section surrounding a dead-zone volume formed between the rotor second axial extension and the stator.

The dead-zone seal section comprises axially extending portions connected to upper and lower radial portions to form a closed sealing circuit.

In an advantageous embodiment, the dead-zone seal section comprises axially extending portions connected to the lower radial portion at one end and to the pump chamber seal at another end to form said closed sealing circuit.

In an embodiment, the pump further comprises a pump chamber seal circumscribing the rotor second axial extension and separating the pump chamber from an external environment.

In an advantageous embodiment, the dead-zone seal section is connected to the pump chamber seal.

In an embodiment, the dead-zone seal section circumscribes at least 30%, preferably at least 40% of a total dead-zone volume within the pump chamber.

In an advantageous embodiment, the dead-zone seal section comprises a radial portion disposed at a distance (h) of less than 20% of the overall height (H) from an end of the second axial extension to the pump chamber seal when the rotor is in a position of maximum fill of the pump chamber.

In an advantageous embodiment, the second valve seal comprises a valve-open seal section circumscribing a fluid inlet or outlet formed in the stator.

In an advantageous embodiment, the seal valve-open section is connected to the pump chamber seal.

In an advantageous embodiment, the seal valve-open section comprises oblique portions connected at one end to a radial portion and at another end to the pump chamber seal.

In an advantageous embodiment, the stator is made of injected polymers, a first polymer for a body of the stator and a second polymer with elastic properties for the valve seals.

In an embodiment, the rotor is made of an injected polymer. In another embodiment, the rotor is made of metal, preferably steel.

Further objects and advantageous features of the invention will be apparent from the claims, from the detailed description, and annexed drawings, in which:

DETAILED DESCRIPTION OF EXEMPLARY EMBODIMENTS

Figure 1:
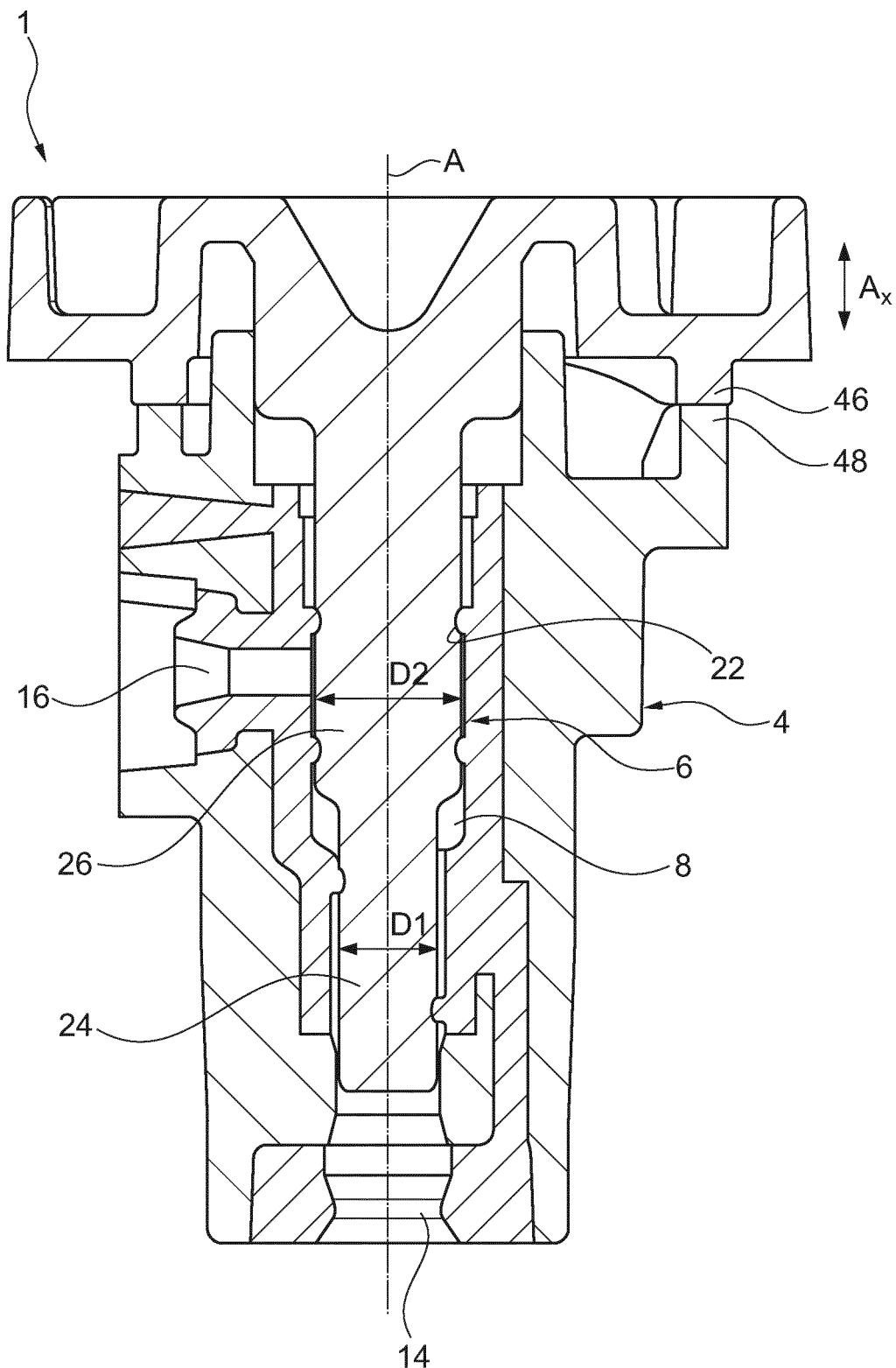
FIG. 1 is a cross-sectional view of a pump (shown without motor drive and without liquid source and liquid outlet connection) according to an embodiment of the invention.

Referring to the figures, a micropump 1 comprises a stator 4 and a rotor 6 driven by a rotary drive (not shown) that imparts a rotational movement on the rotor about an axis of rotation A. The rotor 6 is biased axially, for instance by a spring (not shown), such that a camming system comprising a cam track on the rotor 6 engaging a complementary cam follower 48 on the stator imparts an axial displacement Ax of the rotor relative to the stator as a function of the angular position of the rotor as it turns. The axial and rotational displacement of the rotor relative to the stator causes first and second valves, which will be described in more detail hereinafter, to open and close in order to effect a pumping action. This general functioning principal is per se known and described for instance in EP1803934.

In an embodiment, the pump inlet 14 may be formed at an axial end of the rotor whereas an outlet 16 may be provided towards the end of the rotor comprising the cam. The outlet 16 may extend radially through the stator. The inlet and outlet may be inverted, depending on the rotational direction of the rotor relative to the stator and the valve seals configuration. Moreover, in certain embodiments, the pump may also be configured to be bidirectional whereby the direction of fluid flow depends on the direction of rotation of the rotor. The inlet or outlet formed at an axial end of the rotor may also be directed radially through the stator instead of axially from the end of the stator. The skilled person will appreciate that various fluid channels for the inlet and outlet may be configured according to the connection needs to fluid source and fluid delivery location without departing from the scope of the invention.

The rotor 6 has a first extension 24 having a first diameter D1, and a second extension 26 having a second diameter D2, the first and second diameters having different values. In the illustrated embodiment, the diameter D2 of the second extension 26 is larger diameter than the diameter D1 of the first extension 24. The difference in the first and second diameters coupled with the axial displacement of the rotor defines a pumped volume per revolution of the rotor.

The micropump comprises a first valve V1 formed between the rotor first extension and the stator and a second valve V2 formed between the rotor second extension and the stator. The first and second valves V1, V2, control the opening and closing of the corresponding inlet 14 or outlet 16.

The first valve V1 is formed by a first valve seal 18 mounted on the stator and a first channel 42 mounted on the rotor that is configured to allow liquid communication across the first valve seal when the first valve seal is in an open position, and to not allow liquid communication across the first valve seal when the first valve V1 is in a closed position. The second valve V2 is formed by a second valve seal 20 on the stator 4 and a second channel 44 formed on the rotor 6 that allows liquid communication across the second valve seal when the second valve V2 is in an open position, and to not allow liquid communication across the second valve seal when the second valve V2 is in a closed position. Between the rotor 6 and stator 4 and between the first valve seal 18 and second valve seal 20, a pump chamber 8 is formed.

The first valve seal has a generally oblique configuration, in the sense that it circumscribes the rotor first extension but also extends at least partially in an axial direction. In the illustrated embodiment, the valve comprises oblique portions 50 that define therebetween a valve-open zone 30. For simplicity, the term "oblique" shall be used herein to describe seal sections that extend at least partially in an axial direction (as opposed to a direction that is only in the direction of rotation), the axial direction being parallel to the axis of rotation of the rotor 6. The meaning of oblique as used herein thus encompasses any shape, whether curved, stepped, or linear that includes an axial component. The valve-open zone 30 is generally delimited by a valve-open seal section 32 that comprises the oblique portions 50 and a radial portion 52 bridging the oblique portions. The other side of the oblique portions 50 defines generally a valve-closed zone 31.

The second valve seal also comprises a generally oblique valve that circumscribes the rotor second extension 26 and comprises oblique portions 54 that delimit therebetween a valve-open zone 34. The oblique portions 54 are joined by radial portions 56 in the illustrated embodiment. On the other side of the oblique portions from the valve-open zone 34, is formed a valve-closed zone 38. The valve-closed zone 38 includes a dead-zone 39 that is surrounded by a dead-zone seal section 40.

A pump chamber seal 22 circumscribes the second extension 26 and separates the pump chamber 8 from the pump external environment. The pump chamber seal 22 also has a function of delimiting the valve-open zone 34 because of the connection of the valve-open seal section 36 and in particularly the oblique portions 54 thereof to the pump chamber seal 22.

Figure 2:
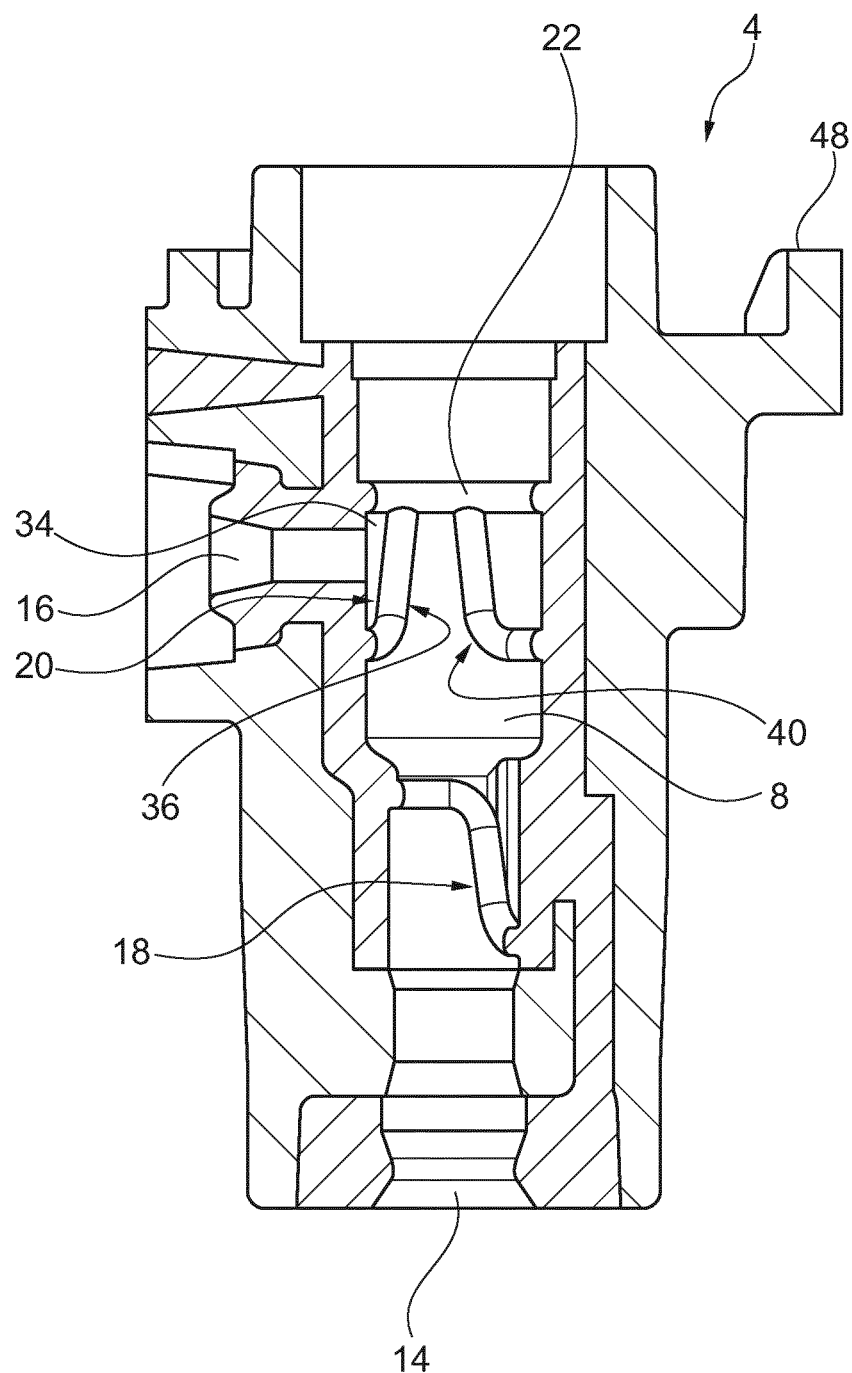
FIG. 2 is a cross sectional view of a stator of the pump according to an embodiment of the invention.

As best seen in FIG. 2, the valve-open seal section 36 that includes a portion of the pump chamber seal 22, the oblique portions 54 and the radial portion 56, surrounds the outlet 16. Thus, when the liquid channel 44 on the second rotary extension 26 crosses over the valve-open seal section 36, liquid communication between the pump chamber 8 and the outlet 16 is opened.

According to the invention, the dead-zone seal section 40 serves to reduce the dead-zone volume of the pump chamber 8.

The volumetric dead-zone is constituted between the rotor 6 and stator 4 around the second rotor extension 26 that has the larger diameter D2. In particular, a gap between the rotor and stator is necessarily present to allow the rotor to move within the stator and for the second valve seal 22 to elastically press against the rotor. A gas bubble, or gas bubbles, can be captured in the dead-zone volume between the stator 4 and rotor second extension 26. During the expulsion phase where liquid is pressed out of the pump chamber 8 through the outlet 16, the presence of a gas bubble in the dead-zone volume can adversely influence the accuracy of the volume of liquid being expelled. This may on a one hand be due to the compressibility of the gas, which due to its varying volume as a function of the pressure, can affect the amount of liquid being expelled and also being drawn into the pump chamber during the filing portion of the pump cycle. Also, the gas bubble may enter the valve-open zone and be expelled from the micropump during normal operation, which may be undesirable, especially in subcutaneous delivery of liquid in a medical application. The dead-zone seal section 40 according to the invention surrounds a large portion of the dead-zone volume 39 and during the liquid expulsion phase of the pump cycle is sealed off from the pump chamber 8 such that gas present in the dead-zone is not in fluid communication with the pump chamber 8, and thus does not influence the accuracy of the pump expelling phase.

The dead-zone seal section 40 in the illustrated embodiment comprises axially extending portions 58 connected to a radial portion 60 at a lower end and a radial portion 60' at an upper end to form a closed sealing circuit. The axially extending portions 50 may be inclined with respect to the axial direction to form oblique portions of similar configuration than the valve-open seal section 36 of the second valve, however other forms are possible such as parallel to the axial direction, or non-linear, a main function being to reduce the overall dead-zone volume in communication with the pump chamber 8.

In an advantageous embodiment as illustrated, the radial portion 60' at the upper end may form part of the pump chamber seal 22 such that the axially extending portions 58 are connected to the pump chamber seal 22. The lower radial portion 60 is disposed close to an end 45 of the second axial extension 26, preferably at a distance (h) of less than 20% of the overall height (H) from the end 45 of the second axial extension to the pump chamber seal 22 when the rotor is in a position of maximum fill of the pump chamber.

Figure 3:
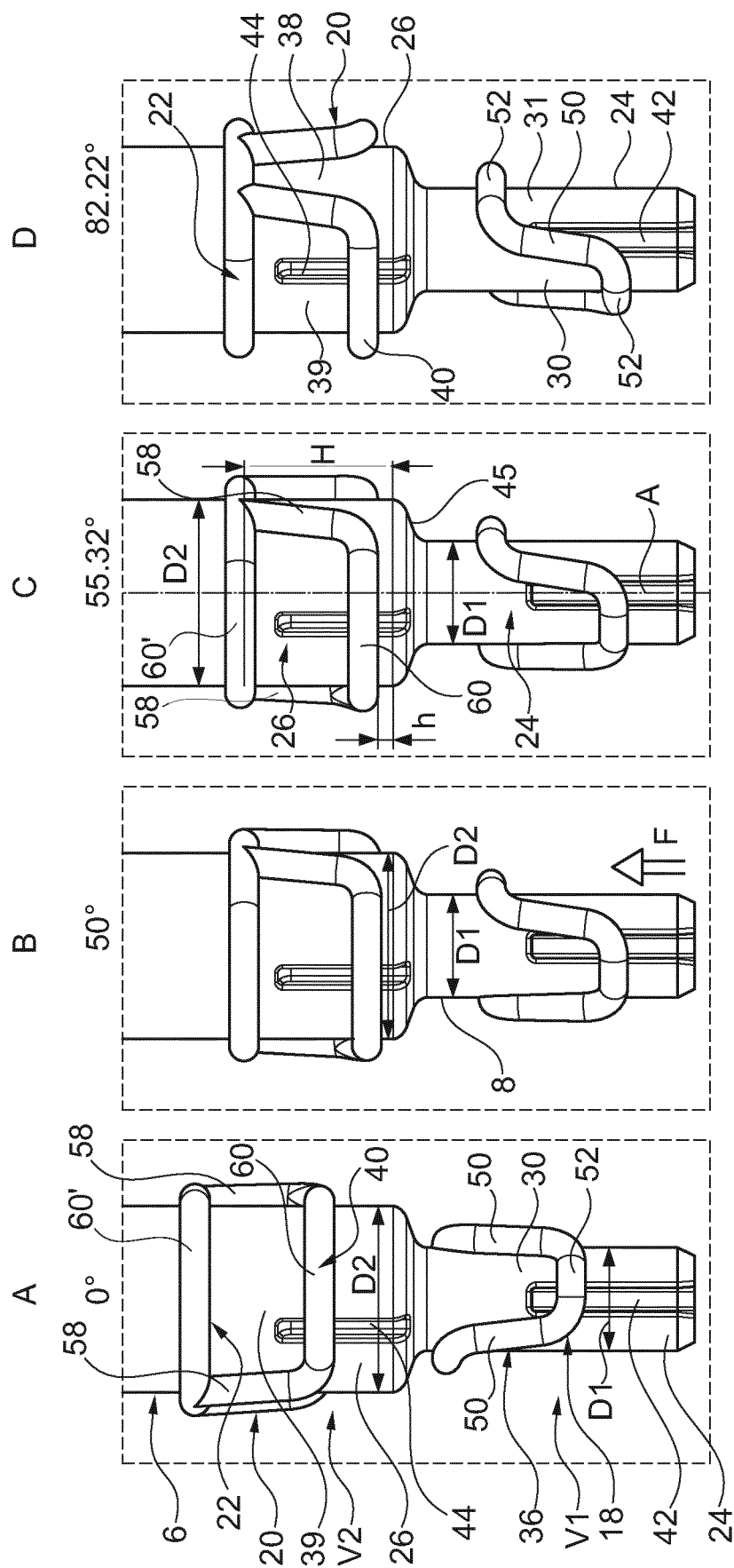
FIGS. 3A to 3M illustrate a rotor and seals of a stator of a pump according to an embodiment of the invention, the FIGS. 3A to 3M illustrating different relative positions between the stator and rotor as the rotor performs a 360 degree revolution relative to the stator during a pumping cycle.

Referring to FIGS. 3A to 3M, various steps in a pump cycle corresponding to one revolution of the rotor are illustrated and will be described. In FIG. 3A, the rotor is in a rotational position relative to the stator such that the first valve V1 is open and the second valve V2 is closed. For ease of description of the subsequent steps we shall consider this position as 0 degrees. In this position, the first channel 42 extends across the first valve seal 18 such that there is liquid communication between the axial inlet side of the pump and the pump chamber 8.

FIG. 3B illustrates the rotor having rotated relative to the stator about 50 degrees. As may be seen, the rotor during the rotation from 0 to 50 degrees has also moved axially relative to the stator in a filling direction F such that the pump chamber 8 is at maximum volume.

In FIG. 3C the rotor is at about 55 degrees and the first valve V1 starts to close. FIG. 3D shows the first valve V1 closed, the rotor being rotated at about 82 degrees. In FIGS. 3C and 3D, the pump chamber 8 is at its maximum fill position.

FIG. 3E shows the rotor at approximately 164 degrees where the first valve V1 remains closed and the second valve V2 starts to open.

There is a certain angular range between which both first and second valves V1, V2 are closed. The angular range between the closing of the first valve V1 and the opening of the second valve V2 illustrated respectively in FIGS. 3D and 3E, provides a security margin ensuring that the first and second valves can never be open at the same time. Direct fluid communication between inlet 14 and outlet 16 is thus prevented, taking into account any manufacturing and operational tolerances.

During the displacement of the rotor when the first valve V1 is open as illustrated in FIGS. 3A to 3D, the second channel 44 extends across the dead-zone seal section 40 and thus opens fluid communication between the rotor chamber and the dead-zone 39. This allows any gas bubbles formed in pump chamber to be captured at least partially in the dead-zone 39. Independently of the capture of gas bubbles, the dead-zone seal section 40 also reduces the overall dead-zone volume in communication with the pump chamber 8, which improves accuracy during the expulsion phase that is illustrated in FIGS. 3E to 3K.

As illustrated in FIG. 3F the second valve V2 is in an open position whereby the second channel 44 crosses the valve-open seal section 36 to establish liquid communication between the pump chamber 8 and the valve-open zone 34. The valve-open zone 34 is in a fluid communication with the outlet 16 as best seen in FIG. 2. The angular position of the rotor relative to the stator, considering FIG. 3A as representing 0 degrees, is at about 180 degrees in FIG. 3F. As the rotor 6 turns while the second valve V2 is open as illustrated in FIGS. 3G to 3J, the rotor is also axially displaced in a pump chamber expulsion direction E such that the large diameter D2 second extension 26 approaches the first valve seal 18 thus reducing the volume in the pump chamber 8. In its lowest axial position as illustrated in FIG. 3J, the second extension 26 of the rotor almost abuts the upper radial portion 52 of the first valve seal 18.

Upon closing of the second valve V2 as illustrated in FIG. 3K, which shows the rotor at an rotational position of about 286 degrees, there is then an angular range during which the first and second valves V1, V2 are both closed. The angular range in the present example is from about 286 degrees to about 324 degrees as illustrated in FIG. 3L which shows the first valve V1 about to open.

FIG. 3M illustrates the end of the full revolution of 360 degrees which thus corresponds to the beginning of the pump cycle illustrated in FIG. 3A.

In the illustrated embodiment, the valve-open seal section 36 is connected to the pump chamber seal 22. In a variant, the valve-open seal section 36 may however be separate and disconnected from the pump chamber seal 22 provided that the valve-open seal section circumscribes entirely the outlet 16 and is configured to engage the second channel 44 on the rotor as it rotates and axially displaces through the angular range corresponding to the open position of the second valve V2.

In a variant (not shown), the dead-zone seal section may also be separate and disconnected from the pump chamber seal 22. However, in the preferred embodiment, the dead-zone seal section 40 is connected to the pump chamber seal 22 such that the upper radial portion of the dead-zone seal section is directly formed by a portion of the pump chamber seal in order to maximize the reduction of the dead-zone volume within the pump chamber and also reduce the overall length of sealing engaging the rotor.

The dead-zone seal section 40 preferably circumscribes at least 30%, more preferably at least 40% of a total dead-zone volume within the pump chamber.

Within the scope of the invention, the first valve seal 18 and a second valve seal 20 may have various configurations and shapes provided that there is an oblique or axial offset in the seal that allows the first and second channels respectively to cross over the respective seals due to the angular and axial displacement of the rotor, to open and close the first and second valves as required during the filing and expulsion phases, without allowing liquid communication directly between the inlet and outlet.

In the illustrated embodiments, the liquid channels 42, 44 are illustrated as grooves extending axially in their respective first and second rotor extensions 24, 26. In a variant however, other liquid channel configurations may be implemented, for instance the channel may not be a groove but buried within the rotor and having orifices on the rotor surface that allow communication across the corresponding seal. It may further be noted that the first valve seal 18 may have a different angular orientation with respective the second valve seal 20 compared to the illustrated embodiment, and that the position of the rotor channel 44, 42 would be adapted accordingly.

The stator may be an injected component for instance an injected polymer with the seal being injected therein for instance in a two-step injection process. The seal may be injected in an elastomeric material as per se known in the art. The rotor 6 may also be injected polymer, the stator and rotor thus forming low cost disposable parts. The rotor 6 may however also be made of a more durable material such as steel or another metal. A metal rotor may be advantageous in certain applications to reduce wear or friction and/or increase dimensional accuracy of the rotor and thus of the pump cycle volume accuracy.

LIST OF FEATURES ILLUSTRATED

Micropump
Stator 4
Inlet 14
Outlet 16
First valve V1
First valve seal 18
Valve-open zone 30
Valve-open seal section 32
Oblique portions 50
Radial portions 52
Valve-closed zone 31
Second valve V2
Second valve seal 20
Valve-open zone 34
Valve-open seal section 36
Oblique portions 54
Radial portions 56
Valve-closed zone 38
Dead-zone 39
Dead-zone seal section 40
Axially extending portions 58
Radial portions 60, 60'
Pump chamber seal 22
Rotor 6
First extension (having a first diameter) 24
First channel 42
Second extension (having a second diameter) 26
Second channel 44
End 45 (connection to first extension)
Pump chamber (formed between the rotor and stator) 8
Axial displacement system 10
Camming system 28
Cam track on rotor 46
Complementary cam follower on stator 48

The invention claimed is:

1. A pump including
a stator,
a rotor slidably and rotatably mounted at least partially in the stator, the rotor comprising a first axial extension having a first diameter and a second axial extension having a second diameter greater than the first diameter,
a first valve formed by a first valve seal mounted on the stator around the first axial extension, in conjunction with a first channel in the rotor that is configured to allow liquid communication across the first valve seal when the first valve is in an open position,
a second valve formed by a second valve seal mounted on the stator around the second axial extension, in conjunction with a second channel in the rotor that is configured to allow liquid communication across the second valve seal when the second valve is in an open position,
a pump chamber seal circumscribing the second axial extension and separating a pump chamber from an external environment, and
the pump chamber formed between the rotor and stator and between the first valve seal and second valve seal,
wherein the stator further comprises a dead-zone seal section surrounding a dead-zone volume formed between the second axial extension and the stator wherein the dead-zone seal section comprises axially extending portions connected to an upper radial portion and a lower radial portion to form a closed sealing circuit.

2. The pump according to claim 1, wherein the dead-zone seal section is connected to the pump chamber seal.

3. The pump according to claim 2, wherein the upper radial portion is formed by a portion of the pump chamber seal such that the axially extending portions connected to the lower radial portion at one end and to the pump chamber seal at another end forms said closed sealing circuit.

4. The pump according to claim 1, wherein the dead-zone seal section circumscribes at least 30% of a total dead-zone volume within the pump chamber.

5. The pump according to claim 1, wherein said lower radial portion is disposed at a distance (h) of less than 20% of the overall height (H) from the end of the second axial extension to the pump chamber seal when the rotor is in a position of maximum fill of the pump chamber.

6. The pump according to claim 1, wherein the second valve seal comprises a valve-open seal section circumscribing a fluid inlet or outlet formed in the stator.

7. The pump according to claim 6, wherein the valve-open section is connected to the pump chamber seal.

8. The pump according to claim 7, wherein the valve-open section comprises oblique portions connected at one end to a radial portion and at another end to the pump chamber seal.

9. The pump according to claim 1, wherein the stator is made of injected polymers, a first polymer for a body of the stator and a second polymer with elastic properties for the valve seals.

10. The pump according to claim 1, wherein the rotor is made of an injected polymer.

11. The pump according to claim 1, wherein the rotor is made of steel.

* * * * *